(12) United States Patent
Zehnder

(10) Patent No.: US 8,202,303 B2
(45) Date of Patent: Jun. 19, 2012

(54) PEDICLE SCREW WITH A CLOSURE DEVICE

(75) Inventor: Thomas Zehnder, Bäch (CH)

(73) Assignee: Spinelab AG, Zug (CH)

( * ) Notice: Subject to any disclaimer, the term of this patent is extended or adjusted under 35 U.S.C. 154(b) by 268 days.

(21) Appl. No.: 12/453,331

(22) Filed: May 7, 2009

(65) Prior Publication Data

US 2009/0287260 A1 Nov. 19, 2009

(30) Foreign Application Priority Data

May 13, 2008 (EP) .................................... 08156089

(51) Int. Cl.
*A61B 17/70* (2006.01)
(52) U.S. Cl. ......... 606/267; 606/264; 606/265; 606/272
(58) Field of Classification Search .................. 606/254, 606/255, 264–272
See application file for complete search history.

(56) References Cited

U.S. PATENT DOCUMENTS

| 5,536,268 | A | 7/1996 | Griss |
| 2004/0260283 | A1 | 12/2004 | Wu et al. |
| 2004/0260284 | A1* | 12/2004 | Parker .............................. 606/61 |
| 2007/0161999 | A1* | 7/2007 | Biedermann et al. ........... 606/61 |

FOREIGN PATENT DOCUMENTS

| DE | 100 05 134 | 8/2001 |
| EP | 1 795 134 | 6/2007 |
| WO | WO 2007/089984 | 8/2007 |
| WO | WO 2007/097905 | 8/2007 |
| WO | WO 2007/122494 | 11/2007 |

OTHER PUBLICATIONS

Translation of DE10005134.*

* cited by examiner

*Primary Examiner* — Thomas J Sweet
*Assistant Examiner* — Megan Wolf
(74) *Attorney, Agent, or Firm* — Jacobson Holman PLLC

(57) ABSTRACT

Pedicle screws with a closure device for receiving and securing a rod made up of a flexible plastic, for stabilization of a vertebral column. The pedicle screws include a screw-in part, a head part with a U-shaped recess formed by two arms and into which the rod to be held is insertable. The U-shaped recess is closable by a locking element. A clamping screw, put into the locking element, presses an insert on the rod and clamps the latter between a first clamping surface and a second clamping surface. The insert is provided with stop faces by which the clamping action against the rod, transmitted to the insert by the clamping screw during the clamping step, is limited. An optimal connection between rod and pedicle screw is thereby obtained.

8 Claims, 6 Drawing Sheets

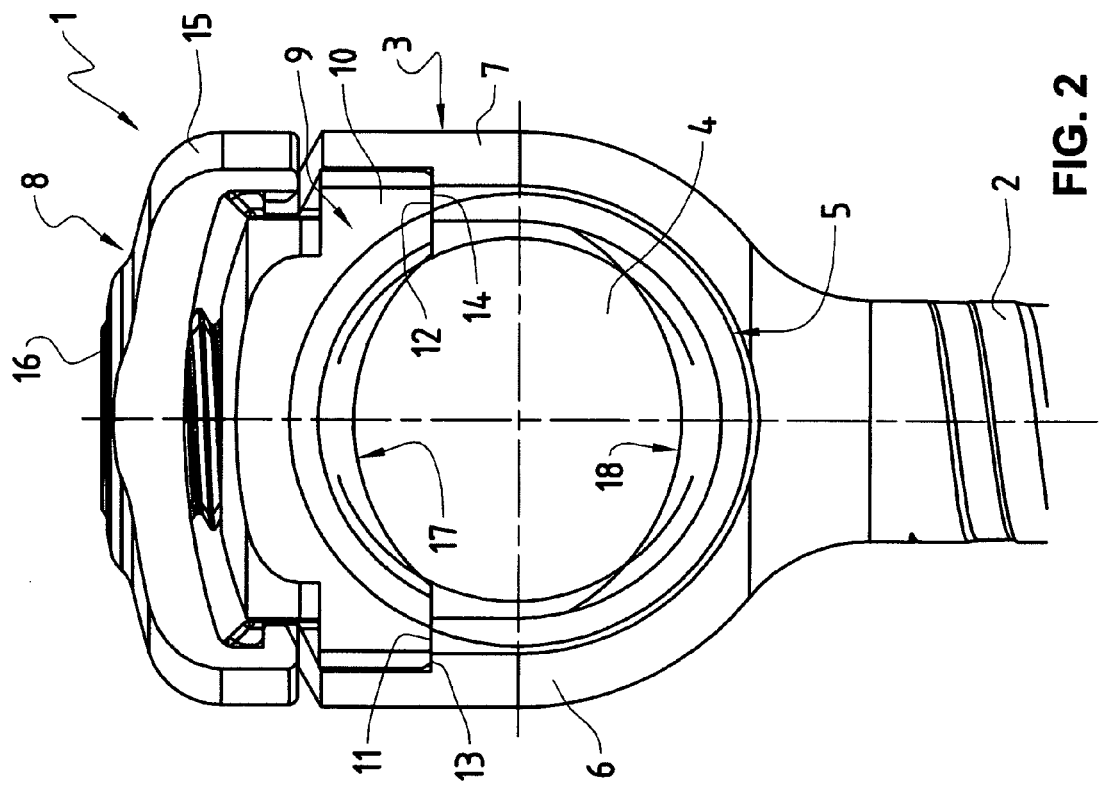
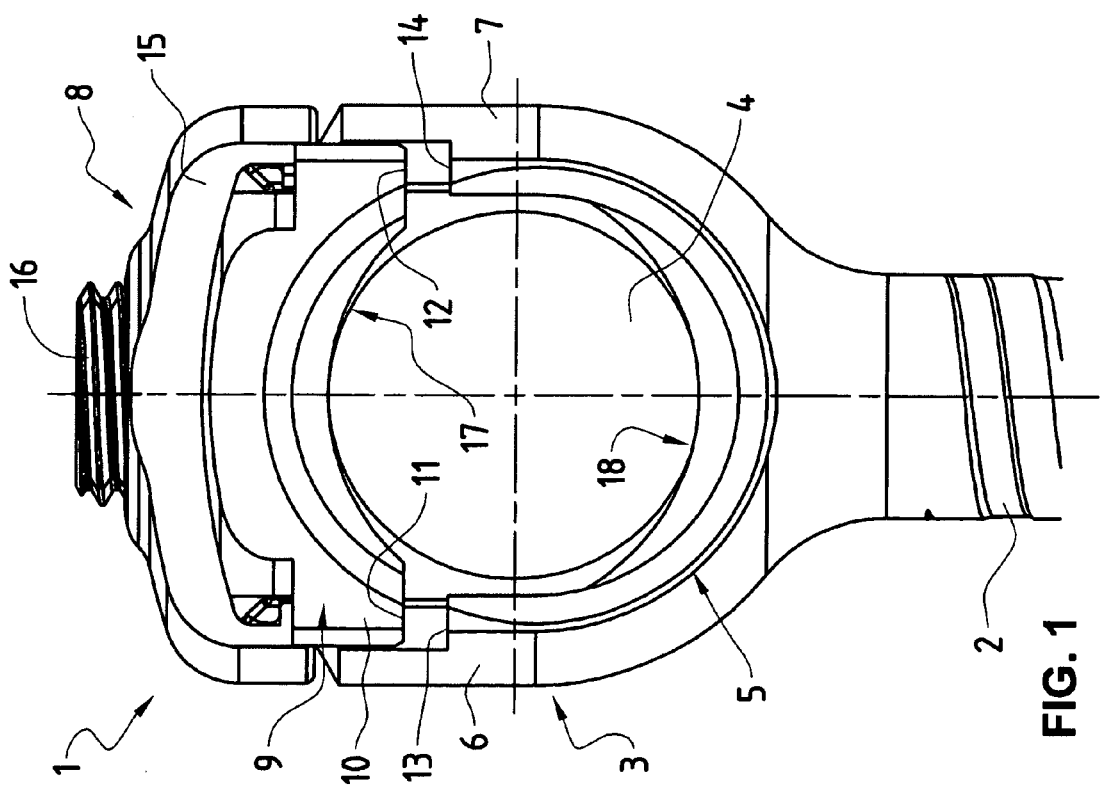

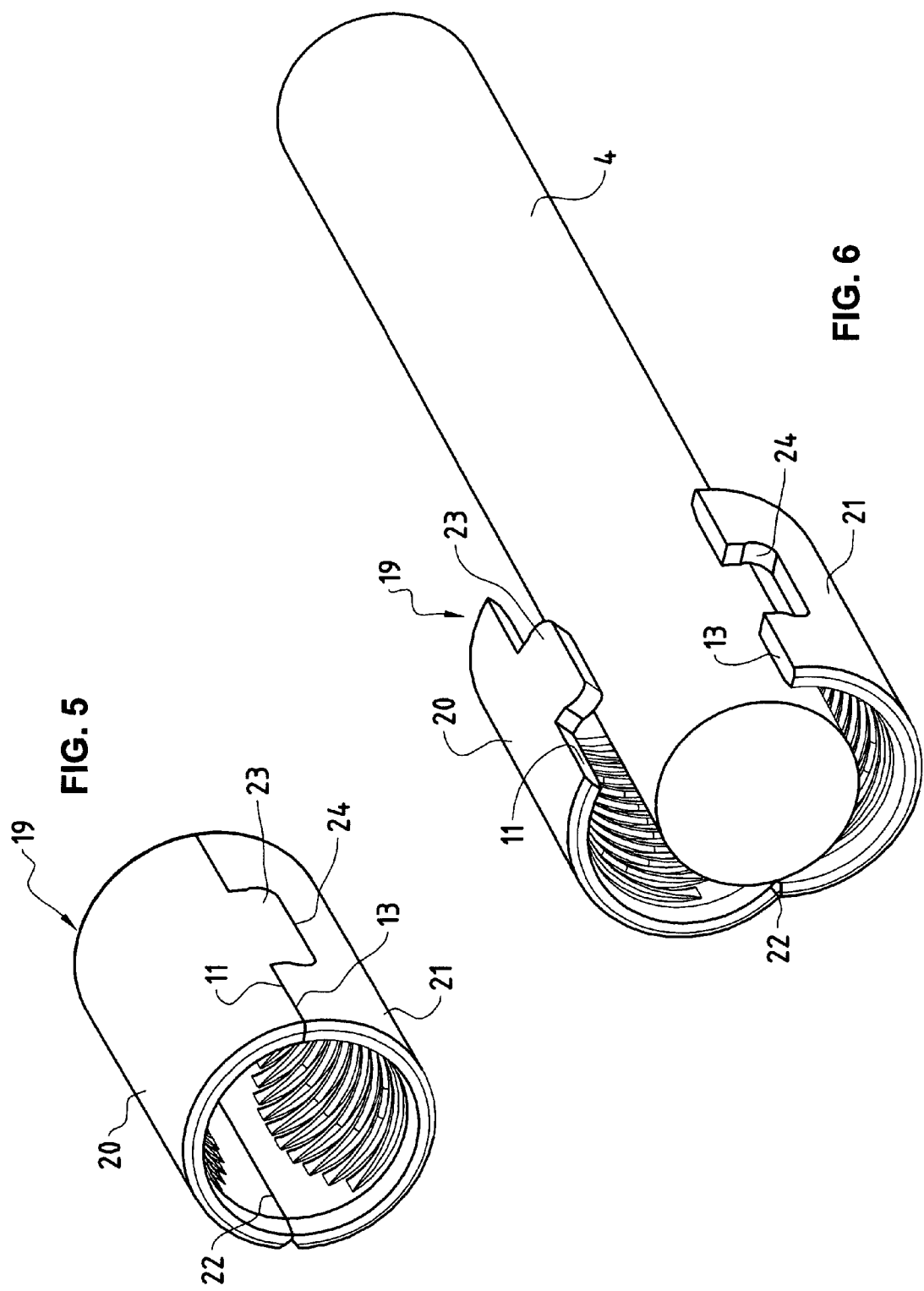

PEDICLE SCREW WITH A CLOSURE DEVICE

This invention relates to a pedicle screw with a closure device for receiving and securing a rod made of a flexible plastic for stabilizing of a vertebral column, comprising a screw-in part, a head part provided on the screw-in part, a U-shaped recess, formed by two arms, disposed in the head part, into which recess the rod to be held is insertable, a locking element with which the U-shaped recess is closable, a clamping screw and an insert which is placeable on the rod and which encloses the latter at least partially, and the rod is held in clamped state between a first clamping surface and a second clamping surface.

Pedicle screws of this kind with a closure device for receiving and securing a rod made of flexible plastic are known in diverse designs. The pedicle screws are each screwed into a vertebral body of a vertebral column to be stabilized of a patient. The rod is inserted in the pedicle screws. The receiving area for the rod of the pedicle screw is closed with a closure device. By means of the clamping screw inserted in the closure device, the rod is firmly clamped in the respective pedicle screw, for which purpose an insert is preferably used between clamping screw and rod. Achieved through the use of a rod made of a flexible plastic is that the individual vertebrae of the thus stabilized vertebral column are not completely locked into position as would be the case with the use of a rod of e.g. steel; a minimal movement between the individual stabilized vertebrae is possible, whereby the vertebrae are prevented from joining together through ossification.

The receiving and securing of the rod made of a flexible plastic in the pedicle screw is decisive for the constant long-term stabilizing support of a correspondingly equipped vertebral column. With the known systems using a rod of flexible plastic, the rod is secured and held in the pedicle screw with great clamping force. The clamping force acting upon the flexible rod is hereby applied in a more or less uncontrolled way by screwing in of the clamping screw. It is well known that flexible plastics under constant pressure tend to yield or flow. Thus, in the cases under consideration, it is possible that the originally applied clamping force is lessened because of plastic flow of the plastic material, and the stability of the device supporting the vertebral column is jeopardized.

The object of the present invention thus consists in designing a pedicle screw with a closure device for receiving and securing a rod made of a flexible plastic for stabilizing a vertebral column in such a way that a predefined clamping force can be applied to the rod and the risk of flow of the plastic material under constant pressure can thereby be limited.

This object is achieved according to the invention in that the insert is provided with stop faces by means of which the clamping action against the rod, transmitted by the clamping screw to the insert during the clamping step, is limited.

Achieved with this design is that the clamping force acting upon the rod is predetermined since the insert flexibly deforms the rod to the point where the insert with the stop faces comes to abut; too forceful a clamping of the clamping screw is thereby prevented, and the clamping force acting upon the rod remains constant.

The insert can be designed as a sliding part which is insertable in a guided way between the two arms of the U-shaped recess, which arms are each provided with a shoulder protruding on the inside on which the stop faces of the sliding part support themselves, the first clamping surface being formed by the surface of the sliding part directed toward the rod and the second clamping surface being formed by the bottom of the U-shaped recess in the head part, resulting in an optimal securing of the rod.

The insert can also be formed by a substantially hollow cylindrical sleeve in which the rod is insertable, which sleeve is composed of a first half-shell and a second half-shell, and which two half-shells are able to be clamped with respect to one another via the clamping screw, the stop faces being provided on the first half-shell which are supportable on support surfaces correspondingly provided on the second half-shell. Thus the pedicle screw can be designed very simply. The inner surface of the first half-shell hereby forms the first clamping surface. The inner surface of the second half-shell forms the second clamping surface.

The first half-shell and the second half-shell are preferably connected to each other in an articulated way along a line of separation, and the first half-shell has at least one tab on the side able to be pivoted open, which tab engages in recesses correspondingly provided on the side of the second half-shell able to be pivoted open. Simple manipulation of the sleeve is thereby achieved.

The first clamping surface and/or the second clamping surface in their middle region preferably have at least one bulge protruding toward the rod inserted in the pedicle screw, whereby tension peaks acting upon the rod at the edge of the tension areas can be avoided.

Another advantageous embodiment of the invention consists in that the first clamping surface and/or the second clamping surface are provided at least in part with elevations and/or with depressions. Through the greater deformation in selected areas of the rod in the clamping region better anchorage can be achieved.

The rod insertable in the pedicle screw preferably has a surface at least in part complementary to the clamping surfaces, whereby a formfitting connection is at least partially obtained.

Another advantageous embodiment of the invention consists in that the width of the elevations provided on the clamping surfaces decreases in rod direction toward the peripheral regions and/or the width of the depressions provided on the clamping surfaces increases in rod direction toward the peripheral regions. Achieved thereby is that, with tensile load of the rod, the forces are optimally transmitted to the clamping surfaces of the insert and no tension peaks occur in the peripheral regions.

The rod preferably consists of a polyurethane-based biocompatible plastic, and the pedicle screw with locking element and insert of a titanium alloy.

The rod to be inserted in the pedicle screw can preferably be heated, whereby, on the one hand, a reduction of the flexural rigidity is achieved. On the other hand, the rod having a smooth surface can experience in the clamped state a plastic deformation through the structured surfaces of the clamping surfaces, whereby a formfitting connection is obtained.

Embodiments of the invention will be explained more closely in the following, by way of example, with reference to the attached drawing.

FIG. 1 shows a sectional representation through a pedicle screw with rod inserted and locking element put on, in non-clamped state;

FIG. 2 shows a sectional representation through the pedicle screw according to FIG. 1, in clamped state;

FIG. 5 shows, in a three-dimensional representation, a hollow cylindrical sleeve in the closed state;

FIG. 6 shows, in a three-dimensional representation, the hollow cylindrical sleeve during placement on a rod;

Figure 3:
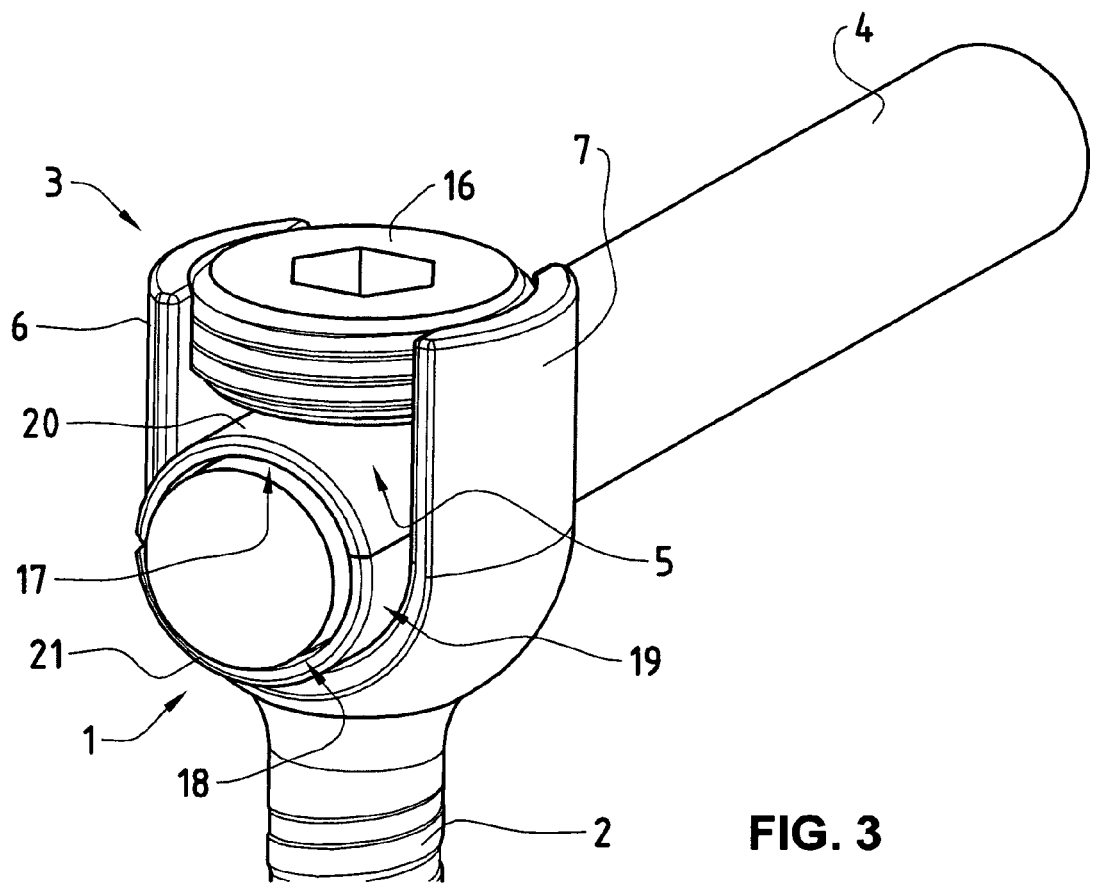
FIG. 3 shows, in a three-dimensional representation, a pedicle screw with inserted rod, in which the insert is designed as hollow cylindrical sleeve.

Visible from FIGS. 1 and 2 is in each case a pedicle screw 1, consisting in a known way of a screw-in part 2 (shown only partially) and a head part 3 provided on the screw-in part 2. In a known way, this pedicle screw 1 can be screwed into one vertebral body each of a vertebral column to be stabilized. The head part 3 is designed to receive and secure a rod 4. The head part 3 has for this purpose a U-shaped recess 5 formed by two arms 6 and 7. The rod 4 can be placed in this U-shaped recess 5.

Placed on the two arms 6 and 7 is a closure device 8, which is interlocked with the two arms in a known way. In the embodiment example shown here, an insert 9 is inserted between the closure device 8 and the rod 4, which insert is designed as sliding part 10, which is placed on the rod in a guided way between the two arms 6 and 7 of the U-shaped recess 5. This sliding part 10 has two stop faces 11 and 12; a shoulder 13 and 14 is provided on each of the two arms 6 and 7.

To secure the rod 4 in the pedicle screw 1, the clamping screw 16, inserted in the locking element 15 of the closure device 8, is tightened. As can be seen from FIG. 2, the sliding part 10 is hereby lowered with respect to the locking element 15 against the rod 4. The clamping screw 16 is turned until the stop faces 11 and 12 of the sliding part 10 come to rest on the respective shoulder 13 and 14 of the two arms 6 and 7. The rod 4 is thus clamped between a first clamping surface 17, which is integrally molded on the sliding part 10, and a second clamping surface 18, which is formed at the bottom of the U-shaped recess 5 of the head part 3.

Achieved through this design of the elements with which the rod 4 is clamped is that the clamping of the rod is always the same, regardless of how forcefully the clamping screw is screwed. Essential is that the two stop faces 11 and 12 support themselves on the shoulders 13 and 14. Too great a clamping of the rod made of a flexible plastic, for example a polyurethane-based biocompatible plastic, is thereby prevented.

Figure 4:
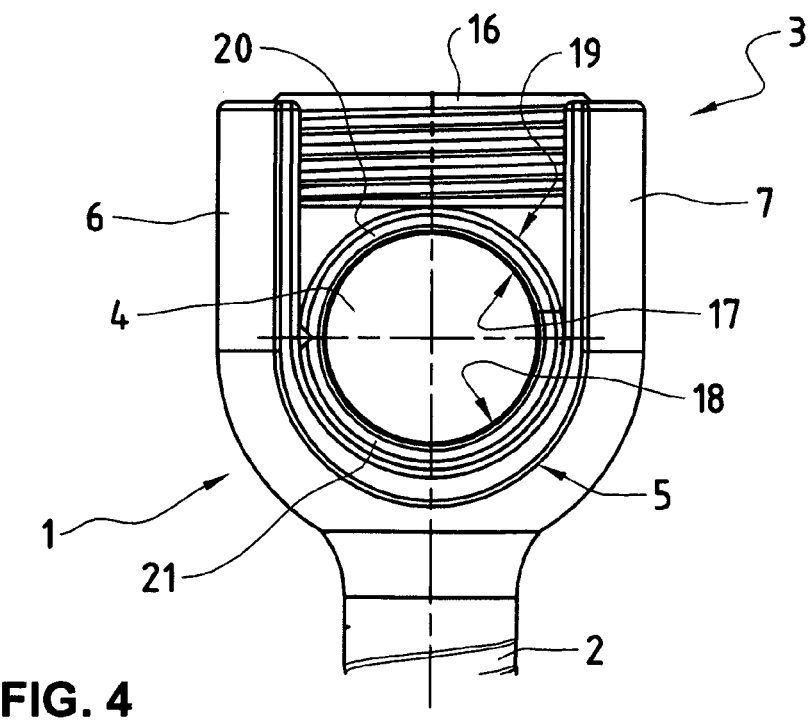
FIG. 4 shows a sectional representation through the pedicle screw according to FIG. 3.

Another embodiment of the present invention can be seen from FIGS. 3 and 4. In the following description, the same reference numerals are used to designate the same parts as in the previous embodiment example. The pedicle screw 1 shown here comprises once again a screw-in part 2 and a head part 3, the screw-in part 2 being screwed once again into a respective vertebral body of a vertebral column to be stabilized. The head part 3 is provided once again with a U-shaped recess 5, formed by two arms 6 and 7. The rod 4 to be held and secured can be placed in the U-shaped recess 5.

Placed around the rod 4 in the region of the U-shaped recess 5 is a hollow cylindrical sleeve 19, which serves as an insert 9. This hollow cylindrical sleeve 19 is composed of a first half-shell 20 and a second half-shell 21, as will still be described in detail.

The rod 4, with the sleeve 19 placed thereon, is inserted into the U-shaped recess 5 of the head part 3 of the pedicle screw 1. Disposed in a known way between the two arms 6 and 7 is a threading into which the clamping screw 16 is screwed. The rod 4 is fixed between the first half-shell 20 and the second half-shell 21 of the hollow cylindrical sleeve 19. The inner surface of the first half-shell 20 forms the first clamping surface 17, while the inner surface of the second half-shell 21 forms the second clamping surface 18. This hollow cylindrical sleeve 19 thus forms the insert 9 by means of which the rod 4 is held in the pedicle screw 1.

The hollow cylindrical sleeve 19 can be seen from FIGS. 5 and 6. The first half-shell 20 and the second half-shell 21 are hereby connected to each other in an articulated way along the one line of separation 22, in a known way. The first half-shell 20 and the second half-shell 21 can thereby be pivoted open about this articulation, as can be seen from FIG. 6. Through this pivoting open, the hollow cylindrical sleeve 19 can be easily put on the rod 4.

A tab 23 is provided on the first half-shell 20 on the side able to be pivoted open, while the second half-shell 21 is provided with a corresponding recess 24. In the pivoted closed state of the hollow cylindrical sleeve 19, the tab 23 comes to be situated in the recess 24. The tab 23 and the recess 24 can thus be designed so that a kind of snap closure is achieved, so that the hollow cylindrical sleeve 19 can be placed on the rod and pivoted closed until the snap closure engages; this snap closure can be designed here such that, with engaged snap closure, the hollow cylindrical sleeve 19 is still displaceable on the rod 4 in longitudinal direction.

The first half-shell 20 has the first stop face 11 on the side able to be pivoted open. The corresponding side of the second half-shell 21 forms the shoulder 13 on which the stop face 11 comes to abut in the clamped state. In this clamped state, as it is shown in FIGS. 3 and 4, the stop face 11 of the first half-shell 20 thus supports itself on the shoulder 13 of the second half-shell 21. The completely clamped state of the rod 4 is thereby reached. A further pressing closed of the sleeve, which is manufactured from a metal alloy, in particular a titanium alloy, does not occur. The rod is thus held in a predetermined state of tension.

Figure 7:
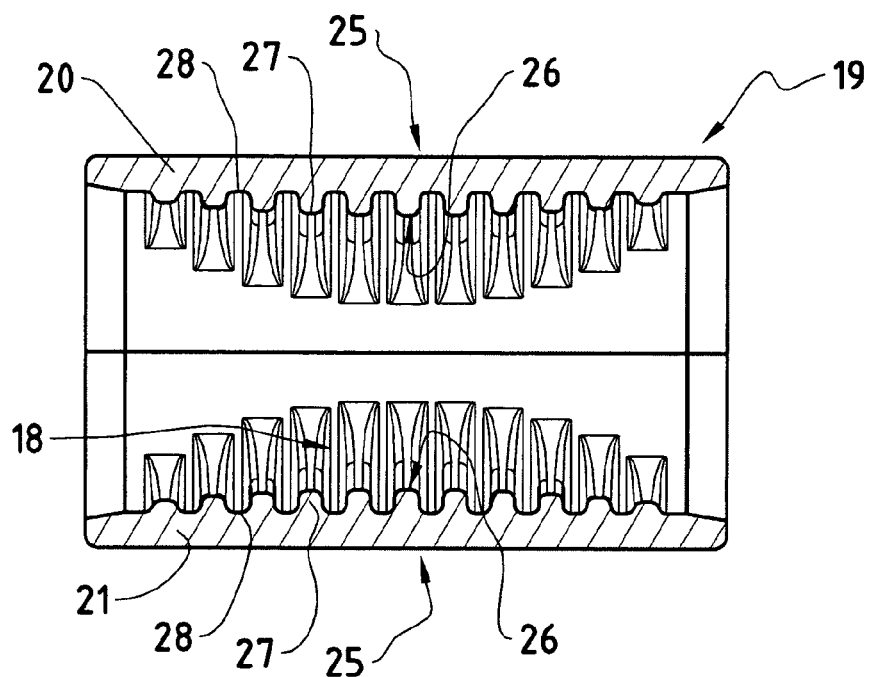
FIG. 7 shows a sectional representation through a hollow cylindrical sleeve.

As can be seen from FIG. 7, the first clamping surface 17 and the second clamping surface 18 of the hollow cylindrical sleeve 19 in their middle region 25 can have a bulge 26 protruding toward the inserted rod 4. Thereby achieved is that the clamped rod is pressed together more firmly in this middle region 25 than in the edge areas, whereby an excessive peak tension in the end region of the two clamping surfaces 17 and 18 is prevented. These bulges 26 can have a smooth surface.

However, they can also be designed with elevations 27 and depressions 28, as is shown in FIG. 7. These elevations 27 and depressions 28 can be designed as ridges and grooves running substantially transversely to the rod direction.

Figure 8:
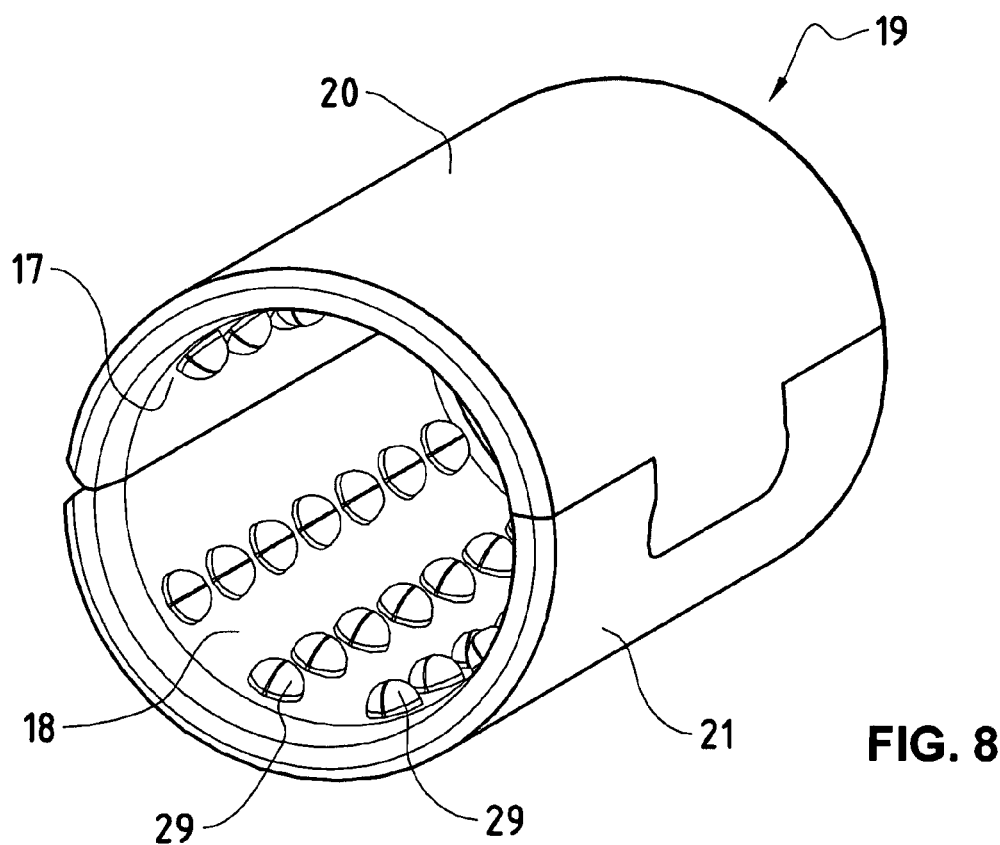
FIG. 8 shows, in a three-dimensional representation, a hollow cylindrical sleeve with elevations provided on the clamping surfaces.

As can be seen in FIG. 8, the first clamping surface 17 and the second clamping surface 18 of the hollow cylindrical sleeve 19 can also be provided with protruding projections 29.

The designs shown in FIG. 7 and FIG. 8 of the first clamping surface 17 and the second clamping surface 18 of the hollow cylindrical sleeve 19 are of course also able to be applied to the first clamping surface 17 and the second clamping surface 18 of the embodiments as they are shown in FIGS. 1 and 2.

Figures 9, 10, 11:
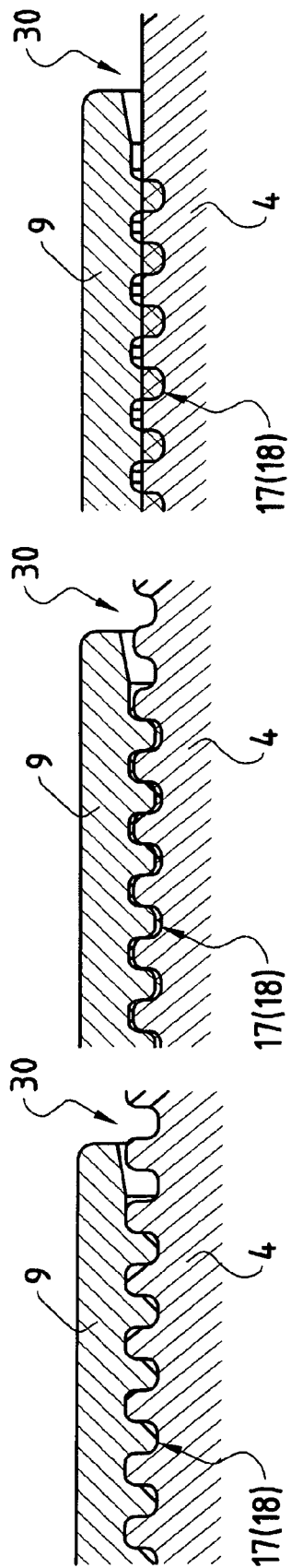
FIG. 9 shows, in section, a clamping surface, provided with ridges and grooves, of an insert and a rod having a complementary surface.
FIG. 10 shows, in section, a clamping surface, provided with ridges and grooves, of an insert, with a rod having a partially complementary surface.
FIG. 11 shows, in section, a clamping surface, provided with ridges and grooves, of an insert and a rod having a smooth surface.

As is shown in FIG. 9, the rod 4 can have a surface 30 which is designed to be complementary to the first clamping surface 17 and to second clamping surface 18, with which the rod is held. A completely formfitting connection is thereby obtained between the two clamping surfaces 17 and 18 and the rod 4.

As can be seen from FIG. 10, the surface 30 of the rod 4 can have a structure partially complementary to the clamping surfaces 17 and 18. A partially formfitting connection is thereby obtained between the clamping surfaces 17 and 18 and the rod 4.

As can be seen in FIG. 11, it is also conceivable to leave the rod with a smooth surface 30, so that in clamped state the elevations of the clamping surfaces 17 and 18 provided with elevations and depressions penetrate at least partially into the surface of the originally smooth rod 4, and the gripping of the rod is thereby improved. The surface structures of the clamping surfaces 17 and 18 must be hereby designed in such a way that the rod surface does not receive any damaging cuts from the elevations, but is only press-fitted.

Figures 12, 13:
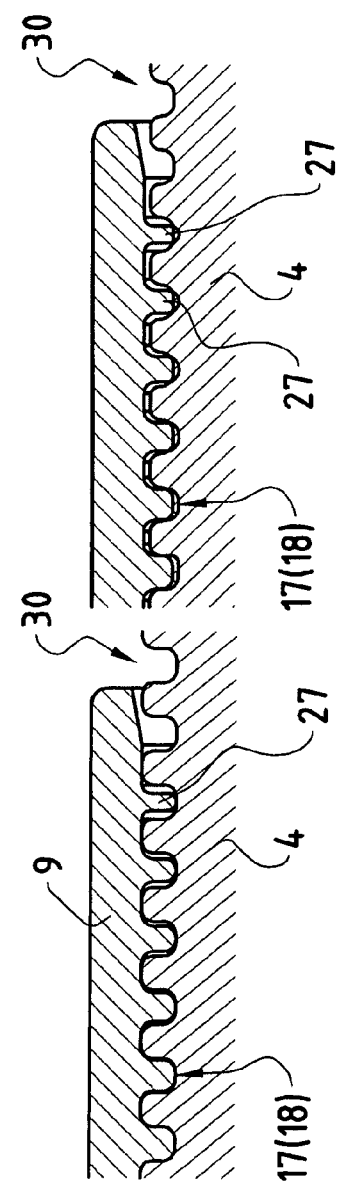
FIG. 12 shows, in section, a clamping surface, provided with ridges and grooves, of an insert and a rod having a complementary surface, the width of the ridges of the clamping surface being decreasing toward the edge area of the insert.
FIG. 13 shows, in section, the insert according to FIG. 12, the rod used here having a surface partially complementary to the clamping surface.

Visible from FIG. 12 is an embodiment in which the surface 30 of the rod 4 has a shape complementary to the design of the clamping surfaces 17 and 18. The elevations 27 of the clamping surfaces 17 and 18 have a width decreasing in rod direction toward the edge regions of the clamping surfaces 17 and 18. Achieved thereby is that a tensile load on the rod 4 is not transmitted to the corresponding clamping body exclusively in the edge region, but instead extends over a relatively great length of the clamping body.

FIG. 13 shows the same design for the clamping surfaces 17 and 18, the rod 4 having however a surface 30 only partially complementary to the clamping surfaces 17 and 18. Here the same effect is achieved, however, as has been described in relation to the design according to FIG. 12.

Figure 14:
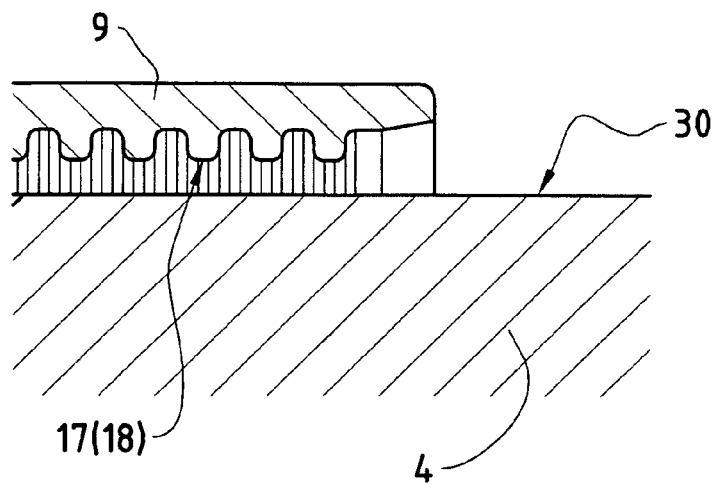
FIG. 14 shows, in section, a rod having a smooth surface and the insert with clamping surface having ridges and grooves, before the clamping step.
Figure 15:
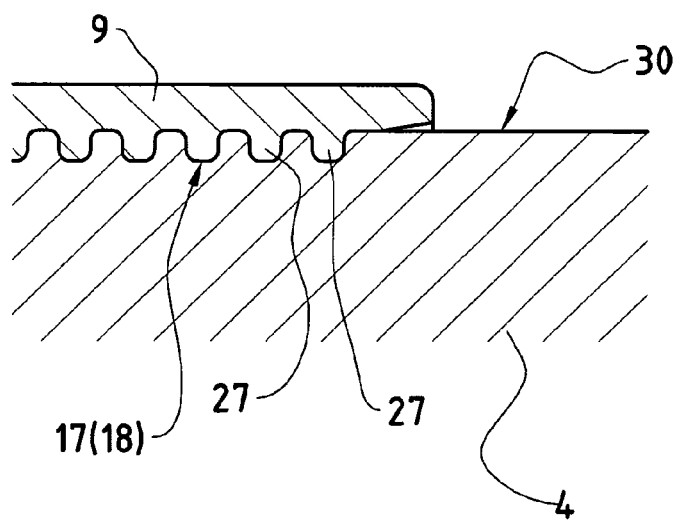
FIG. 15 shows the insert according to FIG. 14 in clamped state, the rod having been heated prior to the clamping step.
Figure 16:
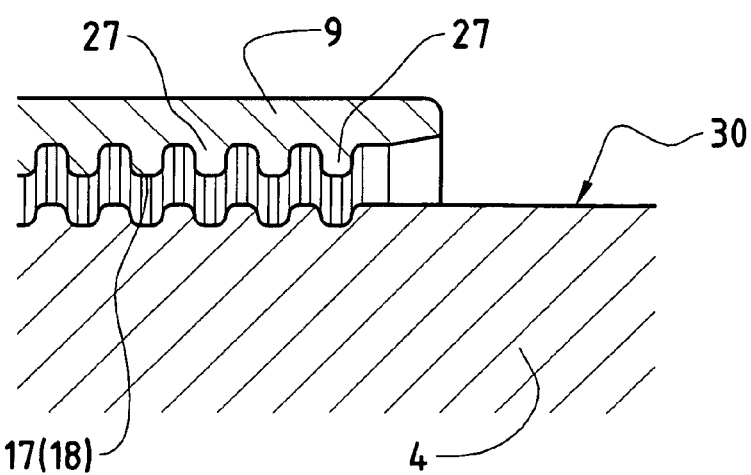
FIG. 16 shows, in section, the insert according to FIG. 14 and FIG. 15, after it has been released again.

FIG. 14 shows a rod 4 with smooth surface 30. The clamping surfaces 17 and 18 are provided with ridges and grooves. The rod 4 here is not yet clamped between the clamping surfaces 17, 18. Before the insertion into the pedicle screws inserted in the vertebral column, the rod 4 can be heated beforehand, for example by water bath, steam, oven or the like. The heated rod thereby allows itself to be bent more easily and thus be more easily inserted into the pedicle screws. Upon clamping of the rod between the clamping surfaces 17 and 18, when the latter are provided with ridges and grooves, the ridges penetrate into the softer surface 30 of the heated rod 4. A formfitting connection is practically obtained thereby between the clamping surfaces 17 and 18 and the rod 4, as can be seen from FIG. 15.

When the rod 4 has cooled off, and the clamping surfaces 17 and 18 are lifted from the surface 30 of the rod, structures remain on the rod surface 30, which structures correspond substantially to the surface structure of the clamping surfaces 17 and 18. This shows that a more or less formfitting connection between rod and clamping surfaces can be achieved by heating of the rod. During heating of the rod, which is made of a polyurethane-based biocompatible plastic, the so-called glass transition temperature (Vicat Softening Temperature) should not be exceeded since the material properties could otherwise be fundamentally changed. This glass transition temperature differs for different materials, as is well known.

With this design according to the invention, an optimal connection is achieved between the rod, consisting of a flexible plastic, and the respective pedicle screws.

The invention claimed is:

1. Pedicle screw system with a closure device and a rod, made up of a flexible plastic, for stabilization of a vertebral column, said pedicle screw system comprising
    a pedicle screw having
        a screw-in part,
        a head part provided on the screw-in part,
        a U-shaped recess, formed by two arms, disposed in the head part, into which recess the rod to be held is insertable, and
        a clamping screw by which the U-shaped recess is closable, and
    a rod,
    a substantially hollow cylindrical sleeve enclosing the rod, said sleeve being composed of a first half-shell and a second half-shell, the first half-shell and the second half-shell being connectable to each other, the two half-shells being clamped against each other via the clamping screw so that the rod in a clamped state is held between a first clamping surface, which is formed by an inner surface of the first half-shell, and a second clamping surface, which is formed by an inner surface of the second half-shell,
    stop faces of the cylindrical sleeve being provided on the first half-shell which are supported on support surfaces correspondingly provided on the second half-shell,
    the first half-shell and the second half-shell being one-piece connected to each other in an articulated way along one line of separation, and the first half-shell having at least one tab on a side able to be pivoted open, the tab engaging in a recess correspondingly provided on a side of the second half-shell,
    whereby during a clamping step, the clamping action against the rod, transmitted to the hollow cylindrical sleeve by the clamping screw, is limited, and for providing a form fitting connection between the clamping surfaces and the rod.

2. Pedicle screw system according to claim 1, wherein the first clamping surface and/or the second clamping surface in their middle region has at least one bulge protruding toward the rod inserted in the pedicle screw.

3. Pedicle screw with a closure device according to claim 1, wherein the first clamping surface and/or the second clamping surface are provided at least partially with elevations and/or with depressions.

4. Pedicle screw system according to claim 3, wherein the elevations are designed as ridges and the depressions as grooves, which ridges and grooves run substantially transversely to the rod direction.

5. Pedicle screw with a closure device according to claim 3, wherein the rod insertable in the pedicle screw has a surface at least in part complementary to the clamping surfaces.

6. Pedicle screw system according to claim 1, wherein the rod consists of a polyurethane-based biocompatible plastic, and the pedicle screw of a titanium alloy.

7. Pedicle screw system according to claim 1, wherein the rod inserted in the pedicle screw is heated.

8. Pedicle screw system with a closure device and a rod, made up of a flexible plastic, for stabilization of a vertebral column, said pedicle screw system comprising a pedicle screw having
- a screw-in part,
- a head part provided on the screw-in part,
- a U-shaped recess, formed by two arms, disposed in the head part, into which recess the rod to be held is insertable, and
- a clamping screw by which the U-shaped recess is closable, and a rod, a substantially hollow cylindrical sleeve enclosing the rod, said sleeve being composed of a first half-shell and a second half-shell, the first half-shell and the second half-shell being connectable to each other, the two half-shells being clamped against each other via the clamping, screw so that the rod in a clamped state is held between a first clamping surface, which is formed by an inner surface of the first half-shell, and a second clamping surface, which is formed by an inner surface of the second half-shell, stop faces of the cylindrical sleeve being provided on the first half-shell which are supported on support surfaces correspondingly provided on the second half-shell, wherein the first clamping surface and/or the second clamping surface are provided at least partially with elevations and/or with depressions, at least one of the width of the elevations provided on the clamping surfaces decreases in a rod direction toward peripheral regions, and the width of the depressions provided on the clamping surfaces increases in the rod direction toward the peripheral regions, whereby during a clamping step, the clamping action against the rod, transmitted to the hollow cylindrical sleeve by the clamping screw, is limited, and for providing a form fitting connection between the clamping surfaces and the rod.

* * * * *